United States Patent [19]

Hemmeter

[11] Patent Number: 4,699,128
[45] Date of Patent: Oct. 13, 1987

[54] THERMALLY ACTIVATED PENILE PROSTHESIS

[76] Inventor: George T. Hemmeter, 4125 Black Point Rd., Honolulu, Hi. 96816

[21] Appl. No.: 876,721

[22] Filed: Jun. 20, 1986

Related U.S. Application Data

[63] Continuation-in-part of Ser. No. 660,216, Oct. 12, 1984, Pat. No. 4,589,405.

[51] Int. Cl.⁴ .............................................. A61F 2/26
[52] U.S. Cl. ...................................................... 128/79
[58] Field of Search ......................................... 128/79

[56] References Cited

U.S. PATENT DOCUMENTS

| | | | |
|---|---|---|---|
| 4,550,720 | 11/1985 | Trick | 128/79 |
| 4,572,168 | 2/1986 | Fischell | 128/79 |
| 4,594,997 | 6/1986 | Hakky | 128/79 |
| 4,625,716 | 12/1986 | Pomeranz | 128/79 |

*Primary Examiner*—Gene Mancene
*Assistant Examiner*—Cary E. Stone

[57] ABSTRACT

This invention is a thermally activated penile prosthesis, consisting of two normally limp cylindrical tubes which when implanted in the corporal cavernosa of an impotent man's penis, and activated, will restore his potency. When heat is applied to the prosthesis, and it reaches a temperature of 98.2 degrees F., the activated chemical gasifies, and causes an entrapped saline liquid to flow into a tubular cavity, causing a stiffening of the normally limp prosthesis. The trapped liquid in a bent, substantially non-stretchable tube, is stiffened. A squeeze operated valve is used to deflate the prosthesis. The saline liquid used in the system will neutralize the hydrocarbon chemical in case there is leakage or accidental rupture of the component parts of the prosthesis, thus making it safe for use by the implantee.

5 Claims, 5 Drawing Figures

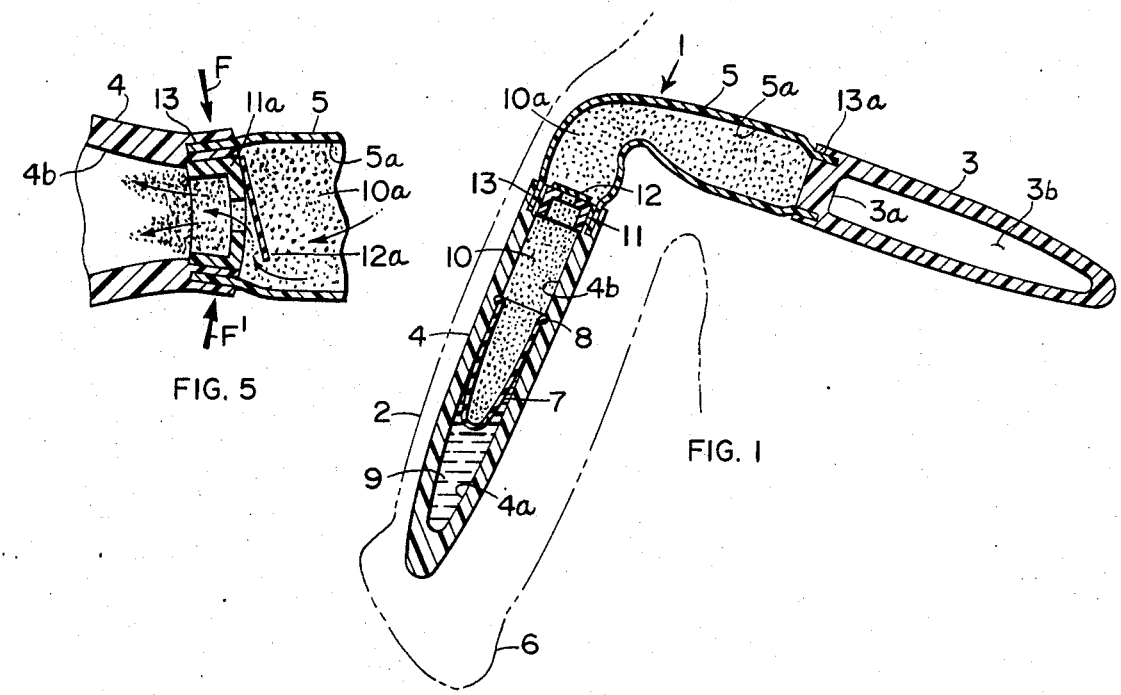
FIG. 5
FIG. 1
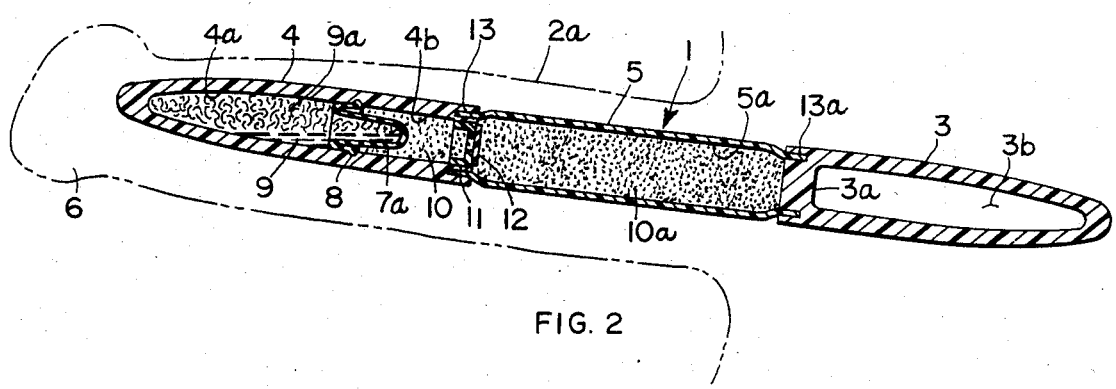
FIG. 2
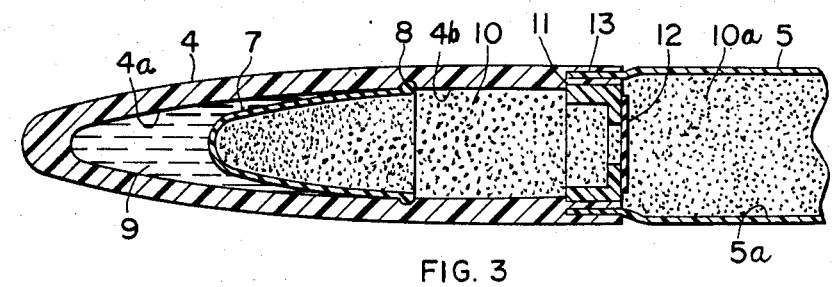
FIG. 3
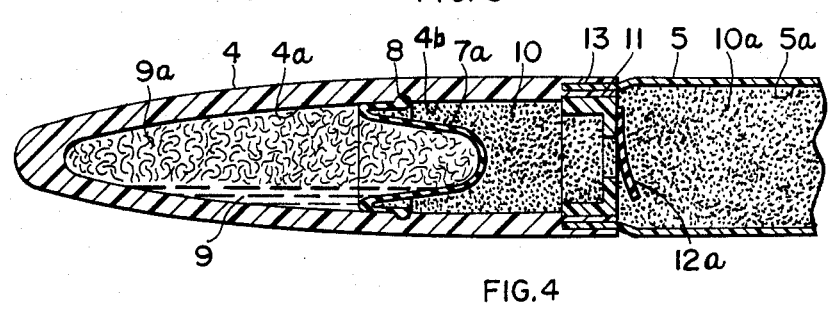
FIG. 4

THERMALLY ACTIVATED PENILE PROSTHESIS

This application is a continuation-in-part of utility application titled "Thermal Activated Penile Prosthesis", Ser. No. 06/660,216 filed Oct. 12, 1984 now U.S. Pat. No. 4,589,405.

BACKGROUND OF THE INVENTION

1. Field of Invention

This invention relates to restoring potency to men who have become impotent due to advanced age or who have had a damaging accident, a prostatectomy, or other similar operation, and to adult men who have been naturally impotent during their adult life.

2. Description of Prior Art

Prior to my invention of thermally activated prosthesis there were two basic types of penile prosthesis in general use: the fixed type using a wire or spring for rigidity, and the inflatable cylinderical type. Each of these prosthesis has its limitations, advantages and disadvantages.

For example, the fixed or rigid type causes a continuous erection of the penis and is obviously a discomfort and may be of some embarrasment to the implantee. The fixed semi-rigid type is foldable at its mid-section and therefore is less obvious and less awkward during normal activities of the implantee.

There are two basic types of inflatable prosthesis: the scrambled type and the self-contained type. Each of these prosthesis gain rigidity by pumping a liquid into the non-distensable tubes implanted in the penis. The scrambled prosthesis is cumbersome and requires more time to implant; the implantee requires more time to convalesce. Essentially the prosthesis consists of a pair of cylinders implanted in the corporal cavernosis of the penis. These cylinders are normally limp but become rigid when inflated with a liquid. To obtain an erection the implantee operates a pump implanted in his scrotum. The pump is supplied with liquid from a reservoir implanted in his belly. To normalize the penis to flacidity, he then operates a deflation valve located in his scrotum, which allows the liquid in the two cylinders to return to the reservoir.

The self contained inflatable prosthesis as its name implies, has a built-in pump, reservoir and deflation valve, together with a supply of fluid. The self contained prothesis is as easy to implant as the fixed or rigid type prothesis but it will not produce either as stiff or as limp a cylinder as with the scrambled inflatable prosthesis.

PRESENT STATE OF THE ART

This invention is a continuation development of my U.S. Pat. No. 660,216 titled "Thermal Activated Penile Prosthesis" filed Oct. 12, 1984 wherein a hydrocarbon chemical is used as a prime-mover to gain rigidity of a penile prothesis implant. Flacidity is obtained by cooling the implanted penis. The use of a hand operated pump is eliminated.

SUMMARY OF THE INVENTION

This invention uses a hydrocarbon liquid (C5H10) placed in the two cylindrical tubes implanted in the penis. When heated above 98.2 Deg. F. the chemical boils, gasifies, and builds-up a pressure in cylinders of the prosthesis. This pressure is the prime-mover on the contained saline liquid causing it to stiffen the penile implant. When the prosthesis is cooled, the hydrocarbon gas condenses to a liquid and the pressure negated. Flaccidity of the penis can then be obtained by operating the deflation valve to release the trapped pressurized saline liquid causing rigidy. The same contained saline liquid is used as a stand-by to neutralize any hydrocarbon chemical leaks, should a rupture occur in the system. The prosthesis cylinders are self-contained. The need for a hand pump to cause an erection, is eliminated.

OBJECT OF THE INVENTION

1. To produce an inflatable prosthesis which will operate without the use of a hand pump.
2. To provide a self contained heat actuated prosthesis which once rigid will remain rigid, until deflated by operating the deflation valve.
3. To provide a built-in, fail-safe system to funtion if a rupture should occur.
4. To provide a self contained prosthesis that is more flacid when deflated, and more rigid when inflated.
5. To provide an inflatable prosthesis whose operation is more natural.

BRIEF DESCRIPTION OF THE DRAWING

FIG. 1 Sectional side view of an implanted, flacid, self-contained, thermally activated prosthesis.

FIG. 2 Sectional side view, of an implanted stiff and rigid, self contained thermally activated penile prosthesis.

FIG. 3 Enlarged sectional view of the gland endpiece of the prosthesis at temperatures below 98.2 degree F.

FIG. 4 Enlarged sectional view of the gland endpiece of the prosthesis at temperatures above 98.2 degree F.

FIG. 5 Enlarged sectional view of the deflation valve squeezed and the flapper valve open.

DESCRIPTION OF A PREFERRED EMBODIMENT

Before explaining the present invention in detail it is to be understood that the invention is not limited in application to the details of construction and arrangement of parts as illustrated on the accompanying drawings; since the invention is capable of other embodiments and of being practiced in various ways and with different thermally activated chemical and neutralizing agents. Also, it is to be understood that the phraseology and terminology employed herein is for the purpose of description and not of limitation.

Refer to the drawings; like numbers and letters to like corresponding parts, are identical thoughout all views.

By way of introduction, this invention is a heat actuated prosthesis, and consists of a pair of cylinderical tubes implanted in the corporal cavernosis of a man's penis. They are approximately 19 mm in diameter and 103 mm in length. They are sized to fit the recepient. When implanted and heated, the prosthesis cylinders become stiff and erection of the penis occurs. When cooled, and the deflation valve is operated, the prosthesis becomes limp; the penis becomes flacid.

FIG. 1 shows a side sectional view of one of a pair of prosthesis cylinders 1 implanted in a penis 2. In this view the prosthesis cylinder 1 is limp and the penis 2 is flacid.

FIG. 2 shows a side sectional view of one of the pair of prosthesis cylinders 1 stiffened and causing the penis 2a to be erected.

In the following description refer to FIG. 1. The prosthesis 1 consist of two semi rigid end-pieces 3 and 4 and connected together with a bendable, non-stretchable tube 5. End-piece 3 is closed off at 3a and the enclosure at 3b is empty. When implanted, the end-piece 3 is near the pelvis. The other end-piece 4 is located near the gland 6 of the penis 2. The inner cavity of end-piece is divided into two chambers 4a & 4b by a gas proof flexible membrane 7. This membrane 7 is attached to the inner wall of end-pieces 4 and 8. The encompassed volume in 4a is filled completely with a hydrocarbon chemical liquid 9 (C5H10), the boiling point of which is 98.2 degrees F., (a temperature slightly lower than body temperature). The remainder of chamber 4 is sealed-off with one-way flapper valve 11. This flapper valve changes its function to a deflation as later described.

Connecting end-pieces 3 and 4, is a non-stretchable, non-distensible, but bendable tube 5. Its volume 5a is completely filled with a saline liquid 10a, even when bent as shown in FIG. 1.

In operation, when heat is applied to the gland, the end-piece 4 is also heated. When the temperature of the hydrocarbon chemical liquid in 4a is heated to and above 98.2 degrees F. it boils and partially gasifies to 9a. The pressure of gas 9a forces diaphram 7 to the 7a position shown in FIG. 2. By so doing the liquid 10 is forced through the flapper-disc 12 of check valve 11, into the chamber 5a of tube 5, causing the non-stretchable non-distensible tube 5a, to straighten and be stiffened. When tube 5 is filled to capacity, the flapper-disc 12 on check valve 11 closes, and the non-compressible liquid 10a in the non-distensible tube 5 is trapped. This makes for a rigid combination and the penis is erected and locked in position as shown in FIG. 2.

To revert to the flacid condition, the erected penis 2a, must first be cooled. When the gaseous hydrocarbon 9a in the end-piece 4 is cooled below 98.2 deg. F., the gas condenses to a liquid, and greatly reduces the volume contained behind diaphram 7a. A partial vacuum is created in cavity 4a.

The check valve 11 now changes its services to a "deflation valve" 11a of FIG. 5. By applying a squeezing force F and F' on the perimeter of this deflation valve 11a, its rubber-like flanged body is deformed inwardly and to the right as shown. The rubber flapper-disc 12a is unseated and the trapped liquid 5a in tube 5 is allowed to flow through opened deflation valve 11a flapper-disc 12a and return to end-piece 4. The penis 2a is now flacid as shown in FIG. 2.

FIG. 3 is an enlarged section of the end-piece 4 with the prosthesis in a limp condition. The hydrocarbon chemical liquid in 9 is contained behind the diaphram 7. The check valve 11 with the flapper-disc 12, as shown closed. Flapper-disc 12 will open by a small differential pressure of fluids in 10 over 10a in chambers 4b and 5a.

FIG. 4 shows an enlarged section of end-piece 4 after heat has been added, to cause the hydrocarbon liquid 9 to boil, and form gas 9a, thereby displacing the diaphram 7 (of FIG. 3) to the right at 7a. This forces the liquid 10 in cavity 4b, to flow through the check-valve 11 by forcing the flapper-disc 12a to the open. The saline liquid 10a then flows into the chamber 5a.

FIG. 5 shows an enlarged section of the deflation check-valve deformed by the squeezing forces F and F'. The body of the valve is deformed to the right by these forces and the flapper-disc 12a is unseated allowing flow of the liquid from right to left. The flapper-disc material 12 is laminated with nylon strands that permit it to bend in a plane, but resist spherical deformation.

In the case of rupture or accidental damage to the prothesis, the chemical added to the saline liquid 10 will neutralize the chemical hydrocarbon 9a and render the mixture harmless to the implantee.

Two cylindrical tubes constitute a self-contained penile prosthesis when implanted in the corporal bodies of a man's penis.

MANUFACTURING PROCEDURE

The chamber 4a is filled with a proper amount of activator chemical charge 9, and sealed. The deflation-valve 11 with the flapper disc 12 assembled is inserted in the end-piece 4. The tube 5 is installed on end-pieces 3 and 4, and vulcanized at points 13 and 13a without any saline liquid in the prosthesis. Care must be taken to keep the charge of hydrocarbon cool during vulcanizing.

The prosthesis is then bent as shown in FIG. 1, and rotated 180 degrees with end-piece 4 pointing upward. A small double-bore-needle is forced alternately into the end-piece 3 and 4. Chilled saline liquid is injected progressively through one bore of the double bored-needle. Entrapped air escapes through the second needle bore. The needle is withdrawn, and its paths are permanently sealed.

The prosthesis is then sterilized by non-heat means and the prosthesis is then packaged and delivered to the hospital, ready for implanting.

I claim as my invention:

1. A self contained penile prosthesis for implanting in the corpus cavernosum of a human male penis consisting of an elongated tubular member comprising of a stiff root end, a normally flaccid non-distensible mid-section, and a penile gland end, said gland end fitted internally with an expandable container filled with a heat sensitive activator fluid being capable of vaporizing when heated to body temperature therby expanding said container under pressure with a liquid and gaseous activation; in a flaccid state a non-compressible fluid fills said mid-section and the portion of the gland end not occupied by said expandable container filled with activator fluid at temperatures under 98.7° F., wherein when said activator fluid is heated to body temperature or higher said activator fluid is partially vaporized thereby extending the expandable container thus forcing said noncompressible fluid to flow under pressure to fill said normally flaccid nondistensible mid-section causing it to stiffen.

2. The prosthesis recited in claim 1 wherein the penile gland is semi-rigid; when said activator fluid is heated to normal body temperature said activator fluid boils and forms a mass which contains a vapor and liquid, thereby expanding said container, which forces the contacted noncompressible fluid contained in the portion of the gland end not occupied by said container, through a check valve located between said mid-section and said gland end whereupon said noncompressible fluid is trapped by said check valve, whereby said mid-section is stiffened.

3. The prosthesis in claim 2, wherein said check valve may be opened by squeezing the prosthesis at the location of the valve whereupon the trapped fluid that stiffens said mid-section is bypassed and returned to said penile gland end and compresses said container, whereby the prosthesis mid-section becomes non-rigid again.

4. The prosthesis in claim 3 wherein when said check valve is held open by squeezing, the prosthesis can be flexed at its mid-section regardless of the action of the activator fluid.

5. The prosthesis recited in claim 1 wherein the activator fluid contains a chemical of either $C_6H_{12}$ of the parafin series which boils at 97.2° F. or $C_6H_{10}$ of the olefin series which boils at 98.2° F.

* * * * *